US011452747B2

(12) United States Patent
Zuscik et al.

(10) Patent No.: US 11,452,747 B2
(45) Date of Patent: Sep. 27, 2022

(54) COMPOSITIONS OF OLIGOFRUCTOSE AND COMMENSAL MICROORGANISMS AND METHODS THEREOF

(71) Applicant: UNIVERSITY OF ROCHESTER, Rochester, NY (US)

(72) Inventors: Michael Zuscik, Rochester, NY (US); Eric M. Schott, Rochester, NY (US); Robert A. Mooney, Fairport, NY (US); Christopher W. Farnsworth, Spencerport, NY (US)

(73) Assignee: University of Rochester, Rochester, NY (US)

( * ) Notice: Subject to any disclaimer, the term of this patent is extended or adjusted under 35 U.S.C. 154(b) by 204 days.

(21) Appl. No.: 16/494,668

(22) PCT Filed: Mar. 14, 2018

(86) PCT No.: PCT/US2018/022292
§ 371 (c)(1),
(2) Date: Sep. 16, 2019

(87) PCT Pub. No.: WO2018/170034
PCT Pub. Date: Sep. 20, 2018

(65) Prior Publication Data
US 2020/0093872 A1   Mar. 26, 2020

Related U.S. Application Data

(60) Provisional application No. 62/471,586, filed on Mar. 15, 2017.

(51) Int. Cl.
| A61K 35/745 | (2015.01) |
| A61P 19/08  | (2006.01) |
| A61K 9/20   | (2006.01) |
| A61K 9/48   | (2006.01) |
| A61K 31/733 | (2006.01) |

(52) U.S. Cl.
CPC .............. *A61K 35/745* (2013.01); *A61K 9/20* (2013.01); *A61K 9/48* (2013.01); *A61K 31/733* (2013.01); *A61P 19/08* (2018.01)

(58) Field of Classification Search
None
See application file for complete search history.

(56) References Cited

PUBLICATIONS

Kolida et al. (British J. Nutr., 87:S193-S197, 2002).*
Pena et al (J. Food Nutr. Res., 2:491-498, 2014).*

* cited by examiner

*Primary Examiner* — Brian Gangle
(74) *Attorney, Agent, or Firm* — Milstein Zhang & Wu LLC

(57) ABSTRACT

The invention provides compositions of oligofructose and specific digestive tract microbes useful for mitigating the negative effects of obesity and/or type 2 diabetes on osteoarthritis, bone fracture healing and immune system function, and methods of preparation and use thereof.

4 Claims, 11 Drawing Sheets

COMPOSITIONS OF OLIGOFRUCTOSE AND COMMENSAL MICROORGANISMS AND METHODS THEREOF

PRIORITY CLAIMS AND RELATED APPLICATIONS

This application is the National Stage of International Application No. PCT/US2018/022292, filed Mar. 14, 2018, which claims the benefit of priority to U.S. provisional application No. 62/417,586, filed Mar. 15, 2017, the entire content of which is incorporated herein by reference for all purposes.

STATEMENT REGARDING FEDERALLY FUNDED RESEARCH OR DEVELOPMENT

This invention was made with government support under TR002001, AR054041, AR061307, AR069655, and AR053459 awarded by the National Institutes of Health. The government has certain rights in the invention.

TECHNICAL FIELD OF THE INVENTION

The invention generally relates to pharmaceuticals and/or nutraceuticals. More particularly, the invention provides compositions of oligofructose and specific digestive tract microbes useful for mitigating the negative effects of obesity and/or type 2 diabetes (hereafter referred to as obesity/T2D) on osteoarthritis, bone fracture healing and immune system function, and methods of preparation and use thereof.

BACKGROUND OF THE INVENTION

Osteoarthritis (OA) is one of the most prevalent diseases in the world, with recent estimates projecting that >250 million people are afflicted globally. In the U.S., OA afflicts 35 million people, with diarthrodial and spinal OA being the most prevalent disease, surpassing the next top four causes of disability combined (heart, pulmonary, mental health and diabetic conditions). In a recent analysis, global medical costs for lower extremity OA exceed $350 billion/year, with the reduced quality of life and physical function of OA patients exerting an additional hidden economic impact that surpasses $50 billion/year. (Murray et al. 2010 *Lancet.* 2013; 381(9871):997-102; Lawrence et al. 2008 *Arthritis Rheum.* 58(1):26-35; CDC, Prevalence and most common causes of disability among adults—United States 2005, MMWR MorbMortalWklyRep. 2009; 58(16):421-6; Salmon et al. 2016 *Osteoarthritis Cartilage* 24(9):1500-8.)

OA is a joint disease of multifactorial etiology characterized by degeneration and loss of articular cartilage and meniscus, subchondral bone sclerosis, osteophyte formation, and synovial hyperplasia. Etiologic complexity and 'whole organ' involvement of multiple tissues within the OA joint during the degenerative process represent significant challenges in the development of disease modifying therapeutic strategies. (Buckwalter et al. 2005 *InstrCourse Lect.* 54:465-80; Goldring et al. 2007 *J Cell Physiol.* 213(3):626-34; Loeser et al. 2012 *Arthritis Rheum.* 64(6):1697-707.)

There are no disease-modifying therapies available for OA at the present time. Over the past two decades, more than a dozen human clinical trials have been performed to test candidate disease modifying OA drugs (DMOADs), none of which have been accepted as a bona fide therapeutic agent. (Kraus et al. 2011 *Osteoarthritis Cartilage* 19(5):515-42; Malfait et al. 2015 *Arthritis research & therapy.* 17:225.)

The only treatment options for these patients before total joint arthroplasty (TKA) at end stage disease are pain reduction through palliative care and physical therapy. Palliative management of OA primarily involves nonsteroidal anti-inflammatory drugs, intraarticular injection of corticosteroids or hyaluronic acid, narcotic-based analgesia including opioids, and joint arthroplasty. Decreased physical activity and the consumption of a high-fat (HF), high-sugar Western diet have contributed to a worldwide epidemic of obesity/T2D. (Zimmet et al. 2001 *Nature* 414(6865):782-7; Ogden et al. 2010 *JAMA* 303(3):242-9.) Health impact of obesity/T2D is traced to a complex systemic metabolic dysfunction which leads to numerous secondary complications, including type 2 diabetes (T2D), heart disease, hypertension, peripheral vascular disease, neuropathy, stroke, and renal failure.

OA is a secondary complication of obesity/T2D that is more prevalent clinically than any of these other complications. Obesity/T2D is a risk factor for both de novo and posttraumatic OA. One consequence of the obesity/T2D epidemic is an increased incidence of OA in both weight bearing and non-weight bearing joints ("Arthritis as a potential barrier to physical activity among adults with diabetes—United States, 2005 and 2007," 2008; Dunbar, Howard, Bogoch, Parvizi, & Kreder, 2009). Sixty-six percent of adults with diagnosed arthritis are overweight or obese. Correlated with this, 55% of patients in the U.S. receiving total knee arthroplasty (TKA) are obese/T2D. Overall, a morbidly obese patient is 33 times more likely to require knee replacement than an individual of normal body mass. (MMWR Morbidity and mortality weekly report. 2008; 57(18):486-9; Dunbar et al. 2009 *The Journal of bone and joint surgery American volume* 91(9):2276-86; Shih et al. 2006 *Am J Prev Med.* 30(5):385-93; Fehring et al. 2007 *J Arthroplasty* 22(6 Suppl 2):71-6; Bourne et al. 2007 *Clin Orthop Relat Res.* 465:185-8.)

Additionally, obesity/T2D is a complication in the context of posttraumatic OA (PTOA), with obese/T2D patients being 4-fold more likely to have OA-inducing injuries. These clinical data establish a link between obesity/T2D and pathogenesis and/or progression of OA and PTOA. (Whittaker et al. 2015 *Osteoarthritis Cartilage* 23(7):1122-9.)

Fractures are a common orthopaedic problem, with over 2 million occurring per year in the U.S. With treatment, most broken bones will heal over a 6-8 week period without clinically relevant delay. Delayed union and nonunion, the failure of a fractured bone to heal, occurs in approximately 5-10% of all fractures. Moreover, delayed and nonunion is associated with significant morbidity. (Amin et al. 2014 *Journal of bone and mineral research* 29(3):581-9; Zura et al. 2016 JAMA Surg. 151(11):e162775; Antonova et al. 2013 *BMC musculoskeletal disorders* 14:42.)

Importantly, multiple clinical studies have demonstrated that obesity/T2D are risk factors for fracture nonunion. This is supported by previous studies demonstrating that mice fed a high-fat diet to induce obesity/T2D have impaired fracture healing. Despite this, little is known about the mechanism(s) that increase the risk of nonunion in obese patients, and there are no accepted therapeutic approaches to address the delay in healing that obese/T2D patients experience. (Zura et al. 2016 JAMA Surg. 151(11):e162775; Rodriguez et al. 2014 *Injury* 45(3):554-9; Brown et al. 2014 *PLoS One* 9(6): e99656.)

Thus, strategies to mitigate the deleterious effect of obesity/T2D on fracture are a critical unmet need.

Obesity/T2D are among the greatest risk factors for infection. Obese/T2D patients have a 25% lifetime risk of developing a foot ulcer, and approximately 56% of these become infected. (Block, 1981; Smith, Weinberger, & Katz, 1987). Furthermore, 20% of these wounds must be treated with a lower extremity amputation. While peripheral vascular disease accounts for the increased risk of foot ulcers in diabetic patients, it does not fully account for the impaired immune response due to the underlying obesity/T2D. (Dowsey et al. 2009 Clin Orthop Relat Res. 467(6):1577-81; Singh et al. 2005 JAMA 293(2):217-28; Smith et al. 1987 Journal of general internal medicine 2(4):232-8; Block 1981 Military medicine 146(9):644-6.)

Obesity/T2D is also associated with increased infection susceptibility following surgery, including abdominal surgery and orthopaedic surgery. Obese patients are also at increased risk of developing community-associated infections such as influenza. Moreover, several studies have demonstrated impaired immune responses in immunized obese patients. (Dowsey et al. 2009 Clin Orthop Relat Res. 467(6):1577-81; Winfield et al. 2016 The American surgeon 82(4):331-6; Jamsen et al. 2012 The Journal of bone and joint surgery American volume 94(14):e101; Mertz et al. 2013 BMJ (Clinical research ed). 347:f5061; Sheridan et al. 2012 International journal of obesity (2005) 36(8):1072-7; Eliakim et al. 2006 Autoimmunity 39(2):137-41.)

There remains an urgent and ongoing need for novel and improved therapeutic approaches that effectively address these issues.

SUMMARY OF THE INVENTION

The invention is based in part on the unexpected discovery that increasing the abundance of bacteria of the genus Bifidobacterium in the gut through the dietary intake of the prebiotic oligofructose resulted in attenuation of several secondary complications of obesity/T2D. As is disclosed herein for the first time, promoting increased abundance of bacteria of the genus Bifidobacterium in the gut rescues several co-morbidities of obesity/T2D.

The present invention thus may fundamentally alter the treatment protocol for OA, fracture repair, and/or bacterial infection as it enables a novel approach that utilizes a combined treatment strategy that includes oligofructose (prebiotic) in a mixture with Bifidobacterium pseudolongum and/or other members of the genus Bifidobacterium (probiotic) to modulate the gut microbiome.

The invention provides the compositions, and methods of use thereof as a therapeutic strategy, of oligofructose (OF) and key digestive tract microbes combined as a dual orally consumed mixture to mitigate the negative effects of obesity and T2D on osteoarthritis (OA), bone fracture healing and immune system function. Specifically, the invention relates to a novel approach that utilizes OF as a dietary supplement that has a systemic biological effect rooted in distinct and specific changes in the populations of resident intestinal microbes. These gut microbiome changes in turn influence numerous tissues, with potent joint health potential and therapeutic efficacy in the OA of obesity/T2D, as well as other health-promoting benefits in impaired bone fracture healing and reduced immune system function that is caused by obesity/T2D. The invention disclosed herein centers on providing OF (as a prebiotic) with microbes from the genus Bifidobacterium (as a probiotic) in a combination formulation to support health claims delineated herein.

Thus, in one aspect, the invention generally relates to a method for treating osteoarthritis, or a related disease or disorder. The method includes: administering to a subject in need thereof a composition comprising oligofructose and microbes from the genus Bifidobacteria, in a single composition or separate compositions, in amounts effective to treat osteoarthritis, or a related disease or disorder thereof.

In another aspect, the invention generally relates to a method for treating bone fracture, or a related disease or disorder. The method includes: administering to a subject in need thereof a composition comprising oligofructose and microbes from the genus Bifidobacteria, in a single composition or separate compositions, in amounts effective to treat bone fracture, or a related disease or disorder thereof.

In yet another aspect, the invention generally relates to a method for treating a disease or disorder of the immune system. The method includes: administering to a subject in need thereof a composition comprising oligofructose and microbes from the genus Bifidobacteria, in a single composition or separate compositions, in amounts effective to treat the disease or disorder of the immune system, or a related disease or disorder thereof.

In yet another aspect, the invention generally relates to a method for improving joint health or bone health. The method includes: administering to a subject in need thereof oligofructose and microbes from the genus Bifidobacteria, in a single composition or in separate compositions, in amounts effective improving joint health or bone health.

In yet another aspect, the invention generally relates to a composition comprising oligofructose and microbes from the genus Bifidobacteria.

In yet another aspect, the invention generally relates to a package or kit comprising oligofructose and microbes from the genus Bifidobacteria.

Definitions

Figure 1:
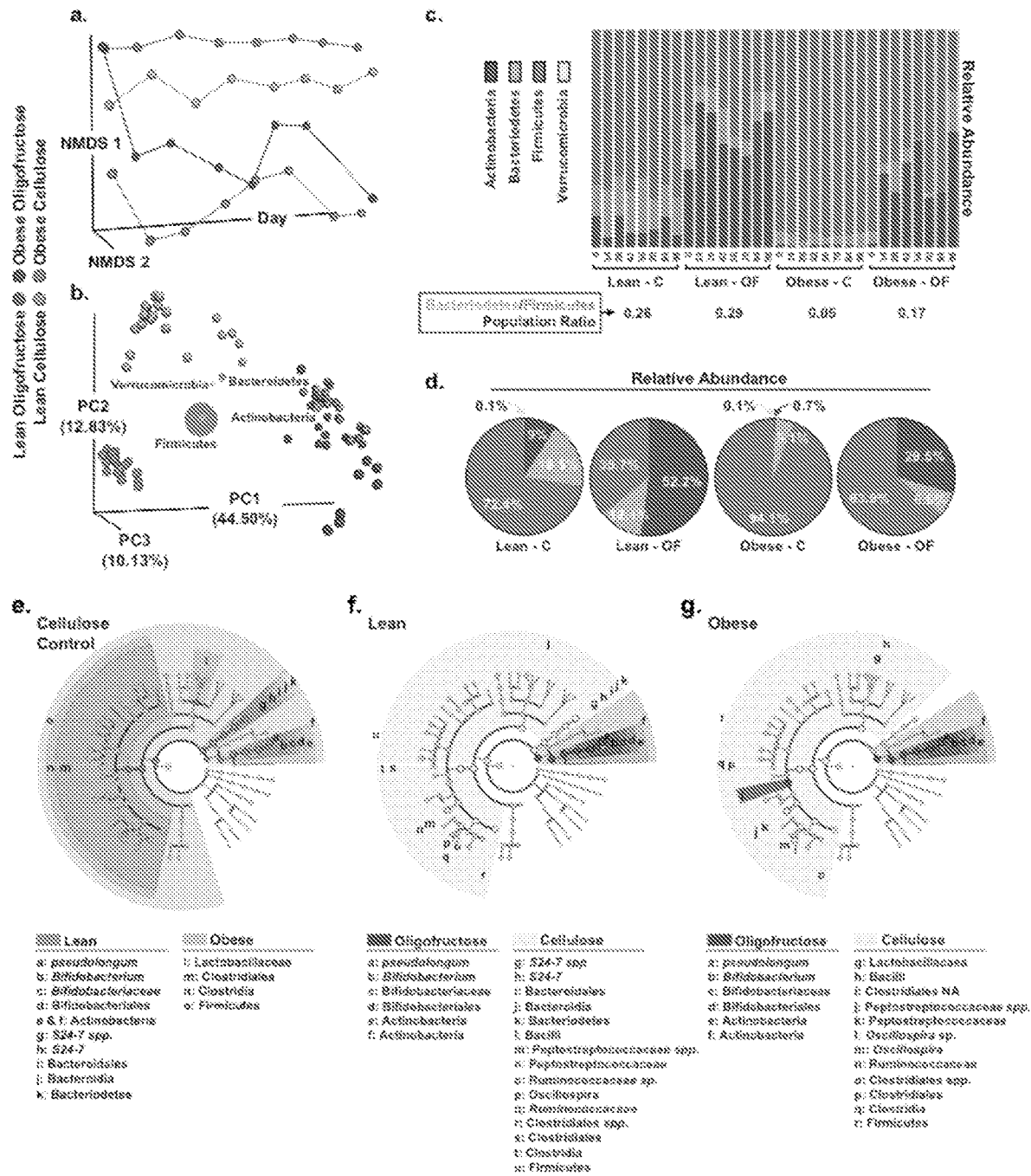
FIG. 1: The gut microbiome is altered by both dietary fat and oligofructose. (a) Representative samples of each experimental group (mice fed low-fat (lean) or high-fat (obese) diets supplemented with control (cellulose [C]) or prebiotic (oligofructose [OF]) fiber) at each time point were computed by taking the average composition of the samples from that group and time point, and nonmetric multidimensional scaling (NMDS) was applied to the pairwise distance matrix between these representative samples. NMDS 1 and 2 comprise the y- and z-axes, portraying more similar samples as closer together and more dissimilar samples as farther apart. The x-axis represents time, showing the progression from the initial pre-treatment samples on the left to the conclusion of the experiment on the right. The representative samples from the obese groups are highly similar prior to treatment, and once treatment begins the obese group receiving oligofructose becomes much more similar to the lean groups, a change that persists for the duration of the experiment. (b) Principal coordinate analysis of all samples from each experimental group, excluding the initial pre-treatment time point. Each point represents one sample and is colored according to diet/treatment, with the distance between samples corresponding to the dissimilarity between them. For each of the six phyla that were identified, a point was defined as the weighted average of the coordinates of the samples that contained that phylum, weighted by the phylum's relative abundance in each sample. These points are indicated by grey spheres, which are scaled according to each phylum's overall relative abundance. (c) The average relative abundance of phyla within in each experimental group at each time point, and the ratio of the relative abundance of Bacteriodetes to Firmicutes within each group over all time points. The four most abundant phyla represent >99.9% of the overall composition of the samples. The ratio of Bacteriodetes to Firmicutes was higher in the lean group than the obese group, and was higher in the prebiotic treated mice than in the controls. (d) The percent abundance of the four most prevalent phyla. (e-g) Cladograms showing taxa that are significantly enriched in one group compared to another by linear discriminant analysis. On the left are taxa that are differentially abundant between lean and obese groups on the cellulose supplemented control diets. In the center are taxa that are significantly different between the treatment and control groups of lean mice. On the right are taxa that are significantly different between the treatment and control groups of obese mice. Colors indicate which group a taxon is enriched in, relative to the other group represented in the same cladogram.

Unless defined otherwise, all technical and scientific terms used herein have the same meaning as commonly understood by one of ordinary skill in the art to which this invention belongs.

As used herein, the term "obese/T2D or obesity/T2D" refers to any of the following disease states: obesity, obesity with concomitant T2D, and T2D.

As used herein, the term "oligofructose" refers to a non-digestible prebiotic dietary fiber scientifically proven to alter the gut microbiome in a beneficial manner.

As used herein, the term "Bifidobacteria" refers to a specific genus of bacteria that resides in the gastrointestinal tract, and is altered by oligofructose. Species in the genus Bifidobacteria include *bifidum, breve, longum, animalis, pseudolongum, lactis, adolescentis, pseudocatenulatum, infantis, bifidus*, and other species classified in the genus *Bifidobacterium*, including those not identified to date. (Famouri et al. *Pediatric Gastroenterology and Nutrition*. 64(3):p. 413-417; Hughes et al. Open Bio. 2017. 7(1); Meng et al. *Gastrointestinal and Liver Physiology*. 2016. 311(4); Sheikhi et al. *Drug Research*. 2016. 66(6): p. 300-305; Cani et al. *Diabetologia*. 2007. 50(11): p. 2374-83; Bernini et al. *Nutrition*. 2016. 32(6): p. 716-719; Reichold et al. *Journal of Nutritional Biochemistry*. 2014. 25(2): p. 118-125; Moratalla et al. *Journal of Hepatology*. 2016. 64(1): p. 135-145; Guo et al. *Journal of Pediatric Gastroenterology and Nutrition*. 2017. 64(3): p. 404-412; Palumbo et al. *Biomedical Papers of the Medical Faculty of the University Palacky*. 2016. 160(3): p. 372-377.

As used herein, the term "*Bifidobacterium pseudolongum*" refers to a specific species of bacteria falling under the genus Bifidobacteria. These bacteria are beneficial to the host and are increased by oligofructose supplementation.

As used herein, the term "effective amount" of an active agent refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the patient.

As used herein, the terms "treatment" or "treating" a disease or disorder refers to a method of reducing, delaying or ameliorating such a condition before or after it has occurred. Treatment may be directed at one or more effects or symptoms of a disease and/or the underlying pathology. The treatment can be any reduction and can be, but is not limited to, the complete ablation of the disease or the symptoms of the disease. As compared with an equivalent untreated control, such reduction or degree of prevention is at least 5%, 10%, 20%, 40%, 50%, 60%, 80%, 90%, 95%, or 100% as measured by any standard technique.

As used herein, the terms "prevent", "preventing", or "prevention" refer to a method for precluding, delaying, averting, or stopping the onset, incidence, severity, or recurrence of a disease or condition. For example, a method is considered to be a prevention if there is a reduction or delay in onset, incidence, severity, or recurrence of a disease or condition or one or more symptoms thereof in a subject susceptible to the disease or condition as compared to a subject not receiving the method. The disclosed method is also considered to be a prevention if there is a reduction or delay in onset, incidence, severity, or recurrence of osteoporosis or one or more symptoms of a disease or condition in a subject susceptible to the disease or condition after receiving the method as compared to the subject's progression prior to receiving treatment. Thus, the reduction or delay in onset, incidence, severity, or recurrence of osteoporosis can be about a 5, 10, 20, 30, 40, 50, 60, 70, 80, 90, 100%, or any amount of reduction in between.

As used herein, the term "pharmaceutically acceptable" excipient, carrier, or diluent refers to a pharmaceutically acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; phosphate buffer solutions; and other non-toxic compatible substances employed in pharmaceutical formulations. Wetting agents, coloring agents, release agents, coating agents, sweetening, flavoring and perfuming agents, and preservatives can also be present in the compositions.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

As used herein, the term "low dosage" refers to at least 5% less (e.g., at least 10%, 20%, 50%, 80%, 90%, or even 95%) than the lowest standard recommended dosage of a particular compound formulated for a given route of administration for treatment of any human disease or condition. For example, a low dosage of an agent that is formulated for administration by inhalation will differ from a low dosage of the same agent formulated for oral administration.

As used herein, the term "high dosage" is meant at least 5% (e.g., at least 10%, 20%, 50%, 100%, 200%, or even 300%) more than the highest standard recommended dosage of a particular compound for treatment of any human disease or condition.

Any appropriate route of administration can be employed, for example rectal, or oral administration. Most suitable means of administration for a particular patient will depend on the nature and severity of the disease or condition being treated or the nature of the therapy being used and on the nature of the active compound.

Solid dosage forms for oral administration include capsules, tablets, pills, powders, and granules. In such solid dosage forms, the compounds and organisms described herein or derivatives thereof are admixed with at least one inert customary excipient (or carrier) such as dicalcium phosphate or (i) fillers or extenders, as for example, starches, lactose, sucrose, glucose, mannitol, and silicic acid, (ii) binders, as for example, carboxymethylcellulose, alignates, gelatin, polyvinylpyrrolidone, sucrose, and acacia, (iii) humectants, as for example, glycerol, (iv) disintegrating agents, as for example, agar-agar, calcium carbonate, potato or tapioca starch, alginic acid, certain complex silicates, and sodium carbonate, (v) solution retarders, as for example, paraffin, (vi) absorption accelerators, as for example, quaternary ammonium compounds, (vii) wetting agents, as for example, glycerol monostearate, (viii) adsorbents, as for example, kaolin and bentonite, and (ix) lubricants, as for example, talc, calcium stearate, magnesium stearate, solid polyethylene glycols, or mixtures thereof. In the case of capsules, tablets, and pills, the dosage forms may also comprise buffering agents. Solid compositions of a similar type may also be employed as fillers in soft and hard-filled gelatin capsules using such excipients as lactose or milk sugar as well as high molecular weight polyethyleneglycols, and the like. Solid dosage forms such as tablets, dragees, capsules, pills, and granules can be prepared with coatings and shells, such as enteric coatings and others known in the art.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other bacterial-compatible solvents, for example, oils, in particular, cottonseed oil, groundnut oil, corn germ oil, olive oil, castor oil, sesame oil, glycerol, polyethyleneglycols, and fatty acid esters of sorbitan, or mixtures of these substances, and the like. Besides such inert diluents, the composition can also include additional agents, such as wetting, suspending, sweetening, flavoring, or perfuming agents.

Materials, compositions, and components disclosed herein can be used for, can be used in conjunction with, can be used in preparation for, or are products of the disclosed methods and compositions. It is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

DETAILED DESCRIPTION OF THE INVENTION

The invention provides a unique approach to treatment of OA, impaired fracture healing, and impaired immune response to bacterial infection as co-morbidities of obesity/T2D. The invention is based on the discovery that increasing the abundance of bacteria of the genus *Bifidobacterium* in the gut through the dietary intake of the prebiotic oligofructose resulted in attenuation of several secondary complications of obesity/T2D. A combination therapeutic composed of oligofructose (prebiotic) and microbes of the genus *Bifidobacterium* (probiotic) is synergistically delivered together to exert beneficial effects in these three clinical situations.

Multiple studies have demonstrated impaired immune cell function in the population, giving rise to a significant risk factor for infection. Investigators and clinicians have increasingly suspected that the microbes residing in the intestinal tract can exert an influence on systemic inflammation and chronic disease. While the gut microbiome has been analyzed in a diet-induced obesity/T2D model of OA, the link between changes in the gut flora and OA disease has not been investigated or established to date. This is also the case in fracture healing and immune system function. (Strandberg et al. 2009 *PloS one* 4(10):e7605; Farnsworth et al. 2015 *Infection and immunity* 83(6):2264-74; Hand et al. 2016 *Trends in endocrinology and metabolism: TEM*. doi: 10.1016/j.tem.2016.08.003; Collins et al. 2015 *Osteoarthritis Cartilage* 23(11):1989-98.)

Thus, it is important to bridge this gap in the understanding of gut microbiome linkage to the comorbid influence of obesity/T2D on OA, fracture healing and immunity. There is an unmet need in all three clinically important situations. Development of a simple method to address the microbiome impact of obesity/T2D can be transformative by providing therapeutic effects in the context on altered immune responses in this context.

The human gut microbiome harbors an immensely diverse array of bacterial species that have coevolved with man over millions of years. The composition of this bacterial ecosystem inhabiting the intestine is dependent in large part on both intrinsic and extrinsic factors, including host genetics and diet. (Moeller et al. 2016 *Science* 353(6297):380-2; Goodrich et al. 2016 *Cell host & microbe* 19(5):731-43; Turnbaugh et al. 2009 *Science translational medicine* 1(6).)

Gut microorganisms benefit the host, playing a large role not only in digestion but in the shaping of the immune system, as well as in growth and development. However, alterations to the normal microbial flora have been implicated in various pathologies, including but not limited to, allergic asthma, obesity, type 2 diabetes, rheumatoid arthritis (RA), and osteoporosis. Despite the known associations with various disease states, the effect of the gut microbiome has not been investigated in the development and progression of osteoarthritis (OA) in obesity and associated type 2 diabetes. (Kau et al. 2011 Nature 474(7351):327-36; Blanton et al. 2016 Science 351(6275).)

Major risk factors for the development of OA include obesity, T2D, and traumatic injury, as 66% of individuals with OA are either obese or obese/T2D, and individuals who experience meniscal damage or ACL rupture have a 10-fold increased risk of OA. (Shih et al. 2006 Am J Prev Med. 30(5):385-93; Gillquist et al. 1999 Sports medicine 27(3): 143-56.)

Studies have shown evidence that obese/T2D patients and mice have impaired innate immune cell function. The bulk of the field has focused on macrophages and neutrophils, demonstrating impaired phagocytosis and bacterial killing despite increased cell recruitment. To date, no studies have been published linking the gut microbiome to functional consequences in fracture repair.

Prebiotics were initially described as a non-digestible food ingredient that beneficially affects the host by selectively stimulating the growth and/or activity of one or a limited number of bacteria in the colon, and thus improves host health. Typically, non-digestible dietary fibers, these polysaccharides are usually derived from plant material and are not digestible by humans, are a source of fermentable nutrients for the bacteria in our intestinal tract. The bacteria in the gut that use these fermentable fibers as a fuel source proliferate to occupy a larger proportion of the microbial flora when an appropriate prebiotic is ingested.

As is first disclosed herein: (1) Dietary intake of oligofructose markedly increased the intestinal abundance of microbes from of the genus *Bifidobacterium*, particularly *Bifidobacterium pseudolongum*; (2) Intestinal inflammation and increases in circulating cytokines, both of which occur in obesity/T2D, was mitigated following oligofructose supplementation and enhancement of the *Bifidobacterium* communities in the gut; (3) The accelerated progression of OA in obesity/type 2 diabetes, including loss of articular cartilage, synovial hypertrophy, osteophyte formation, and chondrocyte hypertrophy were blunted by oligofructose intake; (4) The delayed bone fracture repair in obesity/T2D, particularly the larger callus with its markedly increased adiposity, were rescued by dietary oligofructose; and (5) The more severe and prolonged *Staphylococcus aureus* infection in obesity/T2D was blunted by oligofructose intake.

Treating obese/T2D mice with the prebiotic oligofructose suppressed the progression of OA following traumatic knee injury that otherwise initiates rapid joint degeneration. This improvement in joint status in the oligofructose-treated obese/T2D mice was evidenced by improved overall joint structure, improved OARSI scoring of joint degeneration, reduced tibia and femur cartilage loss, increased numbers of Safranin-O positive chondrocytes, and mitigation of synovial TNF expression. Interestingly, even in lean mice, oligofructose provided some protection against this traumatic injury-induced OA, with an increased number of Safranin-O positive chondrocytes, suggesting increased matrix production. In obese/T2D mice, oligofructose protected chondrocytes from hypertrophy, as evidenced by decreased MMP13 and ColX production, leading to the cartilage protective effects observed by histomorphometry 16s rRNA sequencing revealed that mice supplemented with oligofructose had a marked increase in the abundance of species in the microbial genus *Bifidobacterium*, with *Bifidobacterium pseudolongum*, a commensal gut microbe associated with decreased inflammation, primarily responsible for this increase. An obesity/T2D-related decrease in the ratio of Bacteriodetes/Firmicutes was detected in the high fat-fed (HF) control group, consistent with a proinflammatory shift in gut microbe populations. Supplementation with oligofructose reversed this effect of the HF diet, restoring the Bacteriodetes/Firmicutes ratio to that seen in lean mice. These effects of oligofructose on the gut microbiome in obese/T2D mice were associated with reduced circulating cytokines, reduced macrophage infiltration into the synovium, and remarkably, delayed OA progression.

Also demonstrated herein is that the prebiotic oligofructose reverses both the increase in callus size and adiposity that are characteristic of the obese/T2D mouse fracture phenotype. One commensal bacteria, *Bifidobacterium pseudolongum*, a well-known anti-inflammatory microbe, dominates the gut microbiome following oligofructose supplementation. Concurrently, several gut microbial species that are linked to inflammatory states, including *Lactobacillus helveticus* and *Staphylococcus sciuri*, are suppressed by oligofructose.

These results indicate that oligofructose can revert the pro-inflammatory obese/T2D gut microbiome into the state seen in lean-fed healthy mice, concomitantly rescuing the fracture callus architecture and adiposity defects that are associated delayed fracture repair in obesity/T2D.

In summary, oligofructose-induced changes to the gut microbial flora in obese/T2D mice is chondroprotective and chondroregenerative. Increased beneficial and/or decreased inflammatory microbes provided systemic anti-inflammatory effects, which lead to joint specific protection from macrophage infiltration, inflammation, and chondrocyte hypertrophy, culminating in preservation of articular cartilage. To this point, the role of the gut microbiome in OA initiation and progression has never been studied. This set of experiments opens the door to an immense set of new therapeutic approaches for a disease that has none. More importantly, these therapeutics may not need to be complex antibody or gene therapy approaches. Rather, as it is shown, simple pre- or probiotic approaches with few to no side effects could be implemented to treat one of the most prevalent, costly, and debilitating diseases on the planet.

In one aspect, the invention generally relates to a method for treating osteoarthritis, or a related disease or disorder. The method includes: administering to a subject in need thereof a composition comprising oligofructose in an amount effective to treat osteoarthritis, or a related disease or disorder thereof.

In certain preferred embodiments, the method further includes administering to a subject in need thereof a composition comprising microbes from the genus Bifidobacteria in an amount effective to treat osteoarthritis, or a related disease or disorder thereof.

In certain preferred embodiments, the osteoarthritis is associated with obesity and/or type 2 diabetes.

In certain preferred embodiments, the oligofructose is characterized by a non-digestible dietary fiber suitable for increasing specific bacteria under the genus Bifidobacteria in the gastrointestinal tract and providing beneficial health effects.

In certain preferred embodiments, the Bifidobacteria comprises *Bifidobacterium pseudolongum*.

In another aspect, the invention generally relates to a method for treating bone fracture, or a related disease or disorder. The method includes: administering to a subject in need thereof a composition comprising oligofructose in an amount effective to treat bone fracture, or a related disease or disorder thereof.

In certain preferred embodiments, the method further includes administering to a subject in need thereof a composition comprising microbes from the genus Bifidobacteria in an amount effective to treat bone fracture, or a related disease or disorder thereof.

In certain preferred embodiments, the subject is obese and/or suffers from type 2 diabetes.

In certain preferred embodiments, the oligofructose is characterized by a non-digestible dietary fiber suitable for increasing specific bacteria under the genus Bifidobacteria in the gastrointestinal tract and providing beneficial health effects.

In certain preferred embodiments, the Bifidobacteria comprises *Bifidobacterium pseudolongum*.

In yet another aspect, the invention generally relates to a method for treating a disease or disorder of the immune system. The method includes: administering to a subject in need thereof a composition comprising oligofructose in an amount effective to treat the disease or disorder of the immune system, or a related disease or disorder thereof.

In certain preferred embodiments, the method further includes administering to a subject in need thereof a composition comprising microbes from the genus Bifidobacteria in an amount effective to treat the disease or disorder of the immune system, or a related disease or disorder thereof.

In certain preferred embodiments, the immune system disease or disorder is associated with obesity and/or type 2 diabetes.

In certain preferred embodiments, the oligofructose is characterized by a non-digestible dietary fiber suitable for increasing specific bacteria under the genus Bifidobacteria in the gastrointestinal tract and providing beneficial health effects.

In certain preferred embodiments, the Bifidobacteria comprises *Bifidobacterium pseudolongum*.

In yet another aspect, the invention generally relates to a method for improving joint health or bone health. The method includes: administering to a subject in need thereof oligofructose and microbes from the genus Bifidobacteria, in a single composition or in separate compositions, in amounts effective improving joint health or bone health.

In certain preferred embodiments, the oligofructose is characterized by a non-digestible dietary fiber suitable for increasing specific bacteria under the genus Bifidobacteria in the gastrointestinal tract and providing beneficial health effects.

In certain preferred embodiments, the Bifidobacteria comprises *Bifidobacterium pseudolongum*.

In any of the above methods, and in certain preferred embodiments, the oligofructose is administered daily, thrice weekly, twice weekly, or weekly.

In any of the above methods, and in certain preferred embodiments, the microbes from the genus Bifidobacteria are administered daily, thrice weekly, twice weekly, or weekly.

In yet another aspect, the invention generally relates to a composition comprising oligofructose and microbes from the genus Bifidobacteria.

In certain preferred embodiments, the composition is in the unit dosage form of a tablet, capsule, powder or liquid.

In certain preferred embodiments, the composition has a unit dosage having from about 1 gram to about 20 grams (e.g., from about 1 gram to about 15 grams, from about 1 gram to about 10 grams, from about 1 gram to about 8 grams, from about 1 gram to about 5 grams, from about 1 gram to about 3 grams, from about 2 gram to about 20 grams, from about 5 gram to about 20 grams, from about 10 gram to about 20 grams, from about 2 gram to about 15 grams, from about 5 gram to about 10 grams) of oligofructose.

In certain preferred embodiments, the composition has a unit dosage having from about $10^7$ colony forming units (CFU) to about $10^{12}$ CFU (e.g., from about $10^7$ colony forming units (CFU) to about $10^{11}$ CFU, from about $10^7$ colony forming units (CFU) to about $10^{10}$ CFU, from about $10^7$ colony forming units (CFU) to about $10^9$ CFU, from about $10^8$ colony forming units (CFU) to about $10^{12}$ CFU, from about $10^9$ colony forming units (CFU) to about $10^{12}$ CFU, from about $10^{10}$ colony forming units (CFU) to about $10^{12}$ CFU, from about $10^8$ colony forming units (CFU) to about $10^{11}$ CFU) of microbes from the genus Bifidobacteria.

In certain preferred embodiments of the composition, the Bifidobacteria comprises *Bifidobacterium pseudolongum*.

In yet another aspect, the invention generally relates to a package or kit comprising oligofructose and microbes from the genus Bifidobacteria.

In certain preferred embodiments, the oligofructose is in the unit dosage form of a tablet, capsule, powder or liquid.

In certain preferred embodiments, the microbes from the genus Bifidobacteria are in the unit dosage form of a tablet, capsule, powder or liquid.

In certain preferred embodiments, the package or kit has a unit dosage having from about 1 gram to about 20 grams (e.g., from about 1 gram to about 15 grams, from about 1 gram to about 10 grams, from about 1 gram to about 8 grams, from about 1 gram to about 5 grams, from about 1 gram to about 3 grams, from about 2 gram to about 20 grams, from about 5 gram to about 20 grams, from about 10 gram to about 20 grams, from about 2 gram to about 15 grams, from about 5 gram to about 10 grams) of oligofructose.

In certain preferred embodiments, the package or kit has a unit dosage having from about $10^7$ (CFU) to about $10^{12}$ CFU (e.g., from about $10^7$ colony forming units (CFU) to about $10^{11}$ CFU, from about $10^7$ colony forming units (CFU) to about $10^{10}$ CFU, from about $10^7$ colony forming units (CFU) to about $10^9$ CFU, from about $10^8$ colony forming units (CFU) to about $10^{12}$ CFU, from about $10^9$ colony forming units (CFU) to about $10^{12}$ CFU, from about $10^{10}$ colony forming units (CFU) to about $10^{12}$ CFU, from about $10^8$ colony forming units (CFU) to about $10^{11}$ CFU) of genus Bifidobacteria.

In certain preferred embodiments of the package or kit, the Bifidobacteria comprises *Bifidobacterium pseudolongum*.

The following examples are meant to be illustrative of the practice of the invention, and not limiting in any way.

EXAMPLES

Osteoarthritis

In agreement with previous data, obese/T2D mice in this study developed OA at an accelerated rate following injury compared to lean counterparts, as evidenced by worsened OARSI scores and increased cartilage degeneration in both the femur and tibia. (Mooney et al. 2011 *Arthritis research & therapy* 13(6):R198.)

Figure 5:
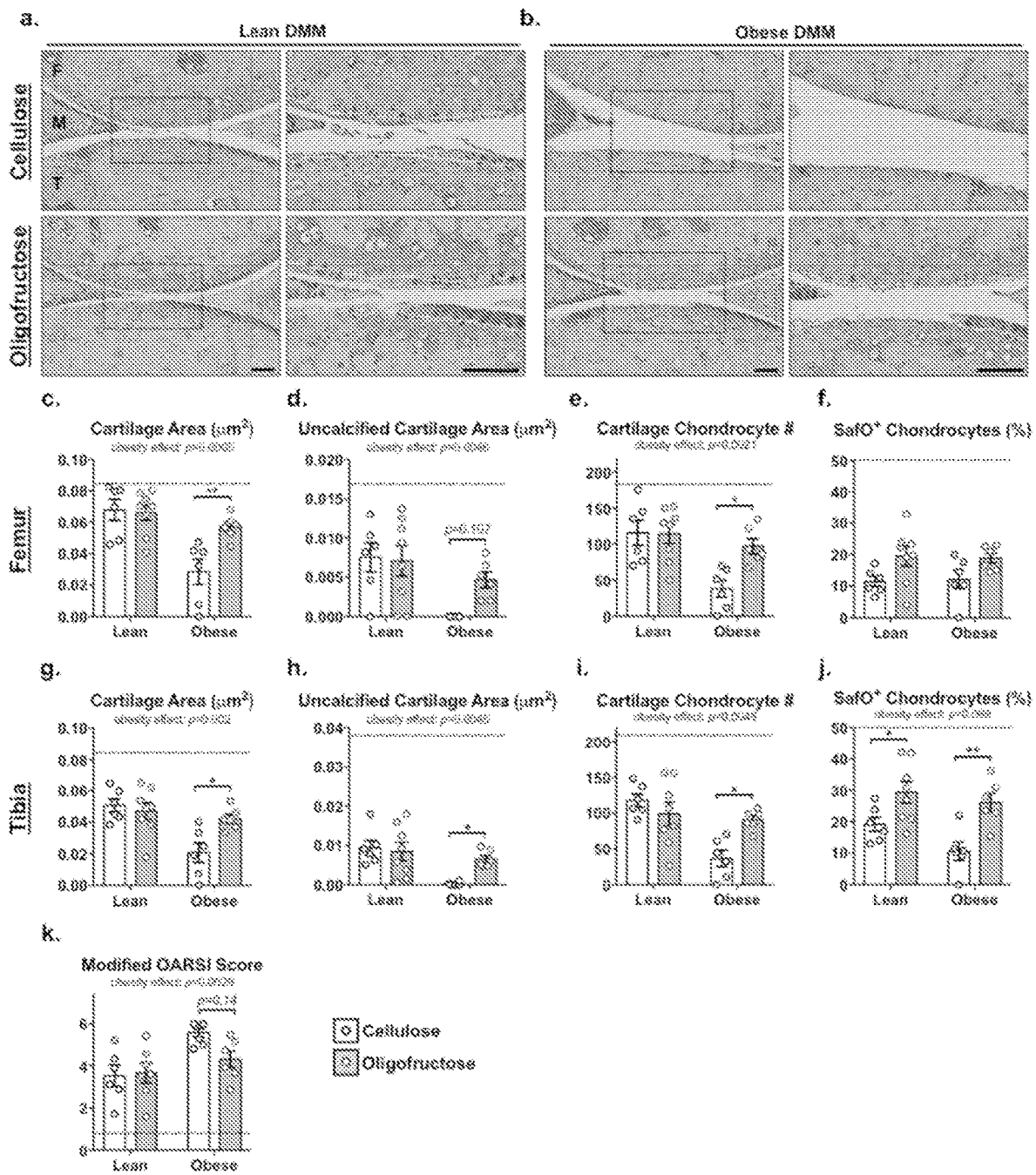
FIG. 5: Oligofructose is chondroprotective in the OA of obesity/T2D. (a, b) Representative Safranin 0/Fast Green stained sagittal sections from the medial compartment of DMM injured joints from lean (a) and obese (b) mice supplemented with cellulose or oligofructose. Joint structures are labeled (F=femur, M=meniscus, T=tibia) and the tidemarks are designated by a yellow dashed line in the high magnification images. Scale bars from both low and high magnification images represent 100 μM. (c-j) Histomorphometric analysis of cartilage architecture using the Osteomeasure System to determine the femur total cartilage area (c), femur uncalcified cartilage area (d), femur cartilage chondrocyte number (e), % femur SafO+ chondrocytes (f), tibia cartilage area (g), tibia uncalcified cartilage area (h), tibia cartilage chondrocyte number (i), and % tibia SafO+ chondrocytes (j). (k) Modified OARSI scoring of Safranin 0/Fast Green stained sections.

Remarkably, despite having equal body mass and adiposity, obese/T2D mice supplemented with oligofructose were protected from this accelerated OA pathology (FIG. 5). These chondroprotective effects of prebiotics in obese/T2D mice were accompanied by the increased presence of Safranin O positive cells, revealing these chondrocytes were anabolic and more actively producing matrix components than control mice (FIG. 5). This is significant because at the time of diagnoses, OA patients typically have lost sizable amounts of cartilage, and merely slowing the continued progression does not alleviate the associated pain and discomfort. Therefore, for an OA therapeutic to truly be effective, it needs to be anabolic, thereby inducing chondrocyte production of matrix components such as proteoglycan to regenerate cartilage.

Figure 2:
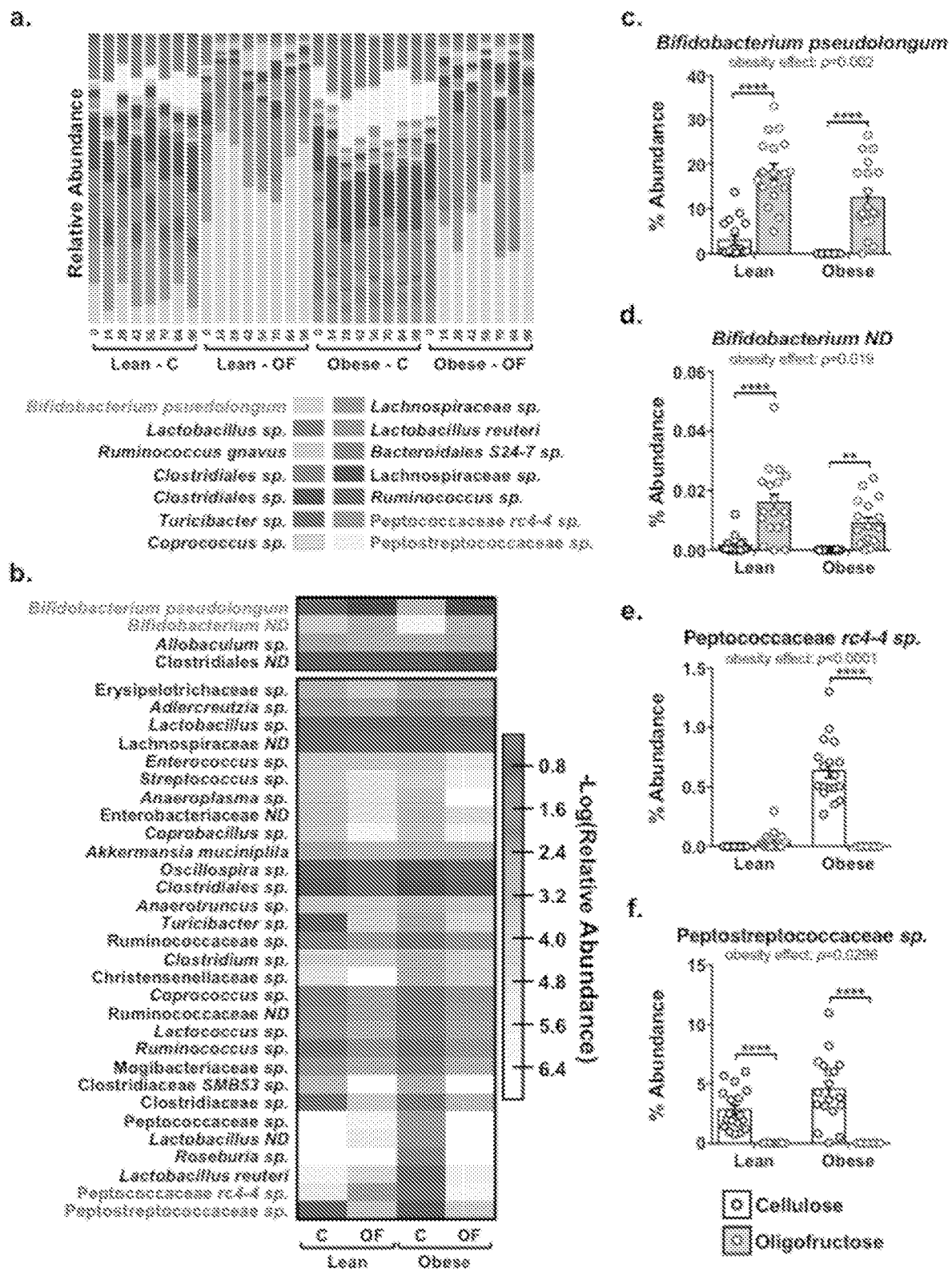
FIG. 2: Species-level analysis identifies *B. Pseudolongum* as a key microbe lost in obesity/T2D and restored following Oligofructose-supplementation. (a) Relative Abundance of various species; (b) Log (Relative Abundance) of various species; (c) Percent Abundance of *Bifidobacterium pseudolongum*; (d) Percent Abundance of *Bifidobacterium* ND; (e) Percent Abundance of Peptococcaceae rc4-4 sp.; (f) Percent Abundance of Peptostreptococcaceae sp.
Figure 3:
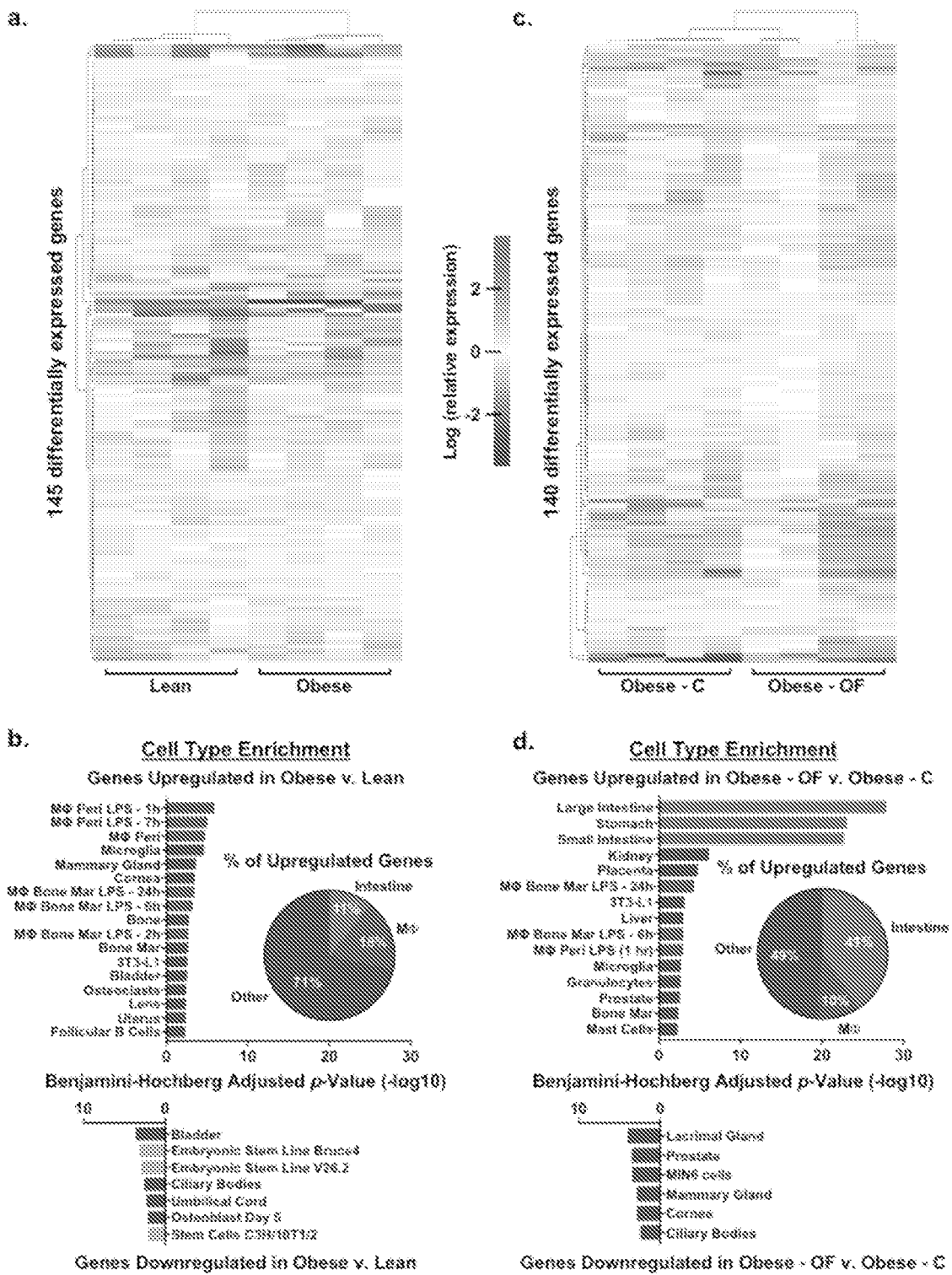
FIG. 3: Analysis of the colon transcriptome reveals a macrophage signature on obesity/T2D, and a support of digestive tract cell phenotype with Oligofructose supplementation. (a) 145 differentially expressed genes; (b) 140 differentially expressed genes; (c) Cell type enrichment in genes upregulated in obese v. lean; (d) Cell type enrichment in genes upregulated in obese—OF v. obese—C.
Figure 4:
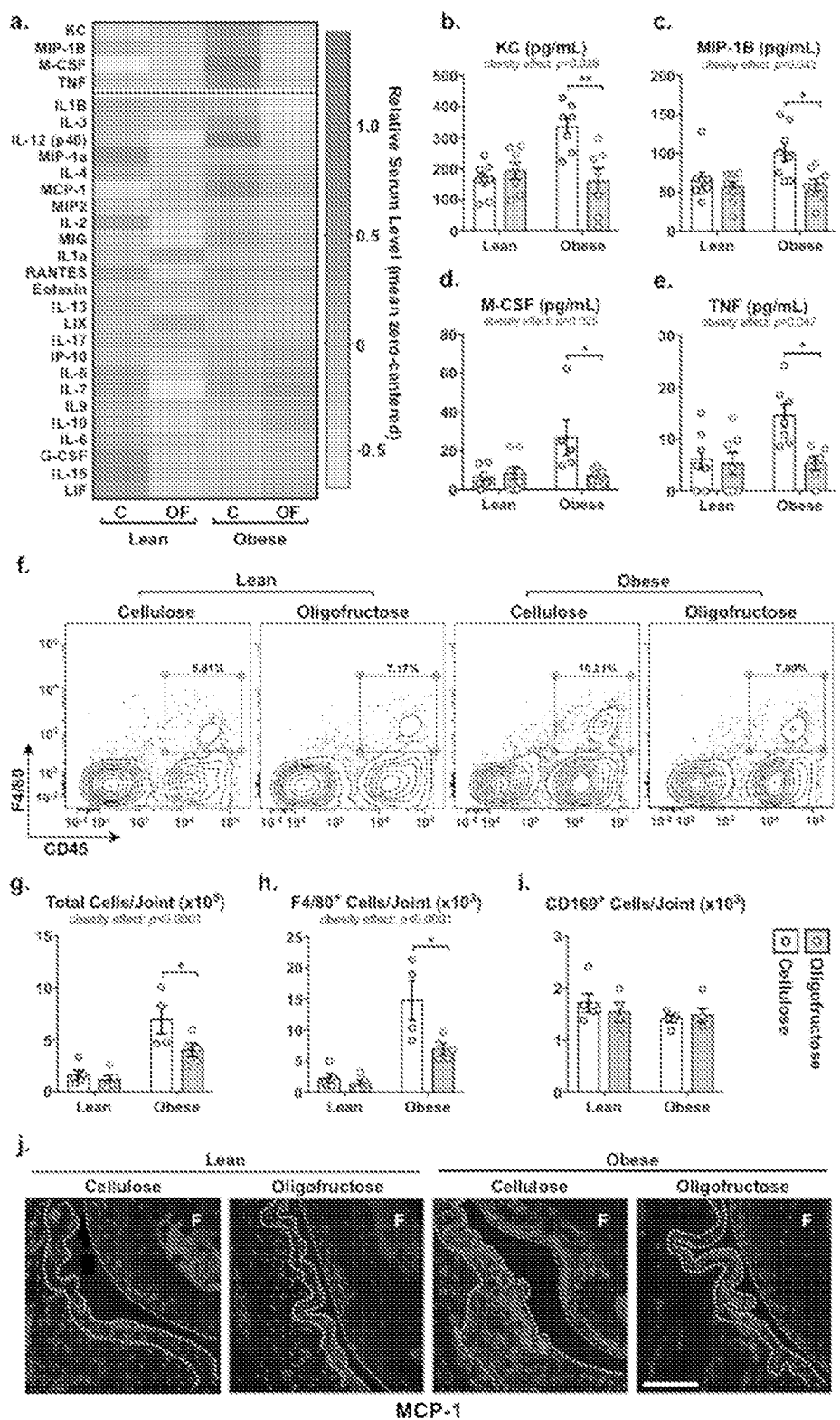
FIG. 4: Induction of systemic and knee joint inflammation in obesity/T2D is resolved in obese mice supplemented with Oligofructose. (a) Heatmap analysis of circulating serum cytokine and chemokine levels from lean and obese mice supplemented with C or OF, with the top four separated by a line indicating the proteins significantly reduced in obese-OF mice compared to obese-C mice. (b-e) Histograms representation of the proteins significantly reduced in obese-OF mice compared to obese-C mice including KC (b), MIP1-β (c), M-CSF (d), and TNF (e). (f) Representative flow cytometry panels of peri-articular soft tissue (PAST) isolated from the four treatment groups, and stained for infiltrating macrophages (F4/80+CD45+). (g-i) histograms depict quantification of total cells (g), infiltrating macrophages (h) and tissue resident CD169+ macrophages (i). (j) Representative immunofluorescent staining of sham-injured joint tissues for the chemokine MCP-1. Scale bar represents 100 μM. Synovial tissue is outlined by yellow dashed lines and the femur is outlined by the blue dashed line.
Figure 6:
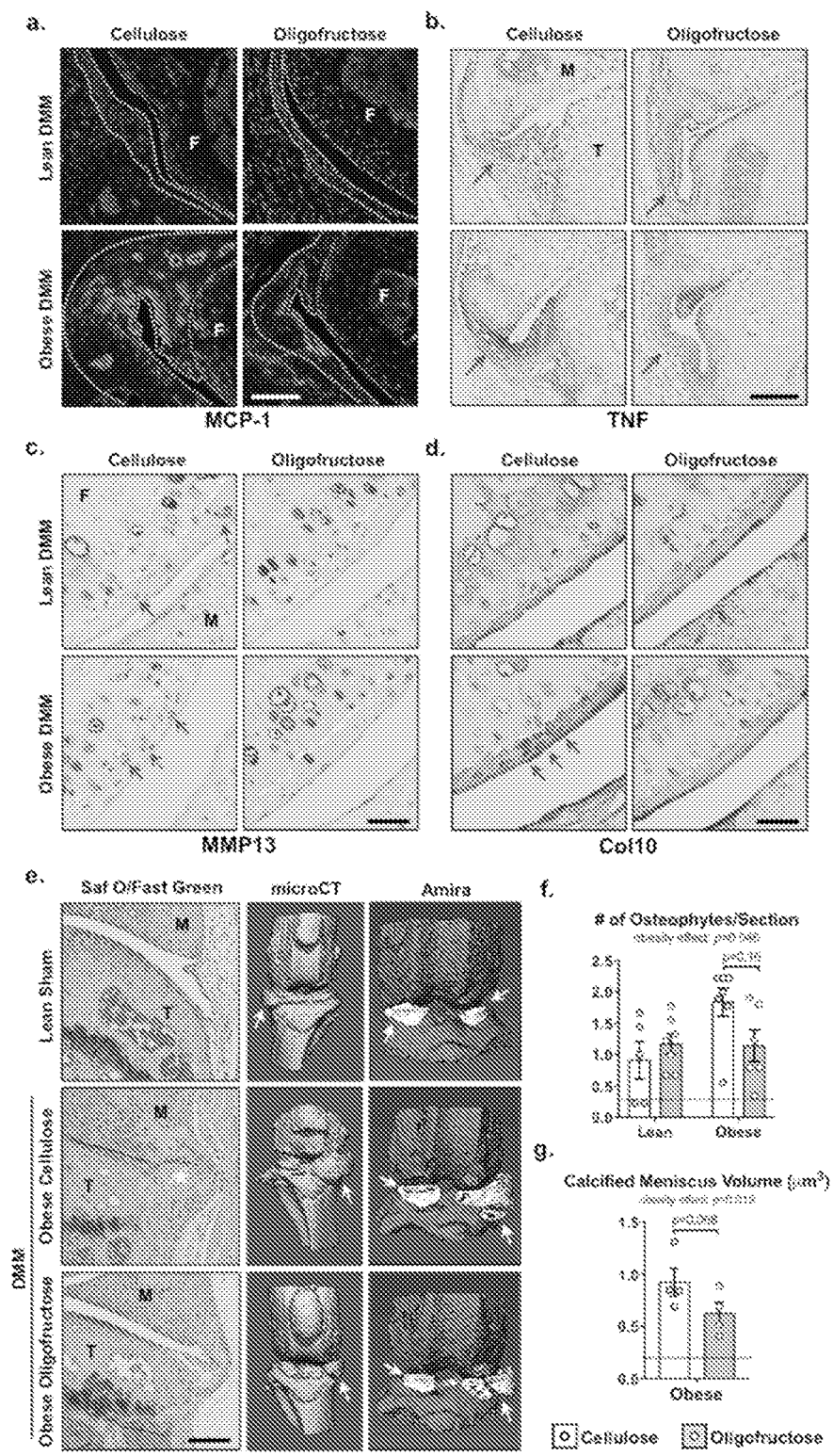
FIG. 6: Obesity/T2D-induced synovial inflammation, chondrocyte hypertrophy and meniscal mineralization/osteophyte formation is reduced following OF supplementation. (a) Representative immunofluorescent staining of synovial tissue from injured joint sections for MCP-1. Yellow dashed lines outline the synovial tissue and blue dashed lines outline the femur (F). Scale bar represents 100 μM. (b) Representative immunohistochemical stained synovial tissue from injured joint sections for TNF. Red arrows indicate area of interest, and joint structures are labeled (M=meniscus, T=tibia). Scale bar represents 200 μM. (c, d) Representative immunohistochemical stained femur articular cartilage from injured joint sections for MMP13 (c) and Col10 (d). Red arrows highlight chondrocyte specific staining of in the uncalcified cartilage. Tidemarks are delineated by yellow dashed lines, and joint structures are labeled (F=femur, M=meniscus). Scale bars represent 50 μM. (e) Representative Safranin 0/Fast Green stained sections, microCT images, and Amira reconstructed images from sham control mice, as well as obese injured mice. Yellow asterisks delineate osteophytes, while white arrows delineate calcified meniscal tissues. Joint structures are labeled (M=meniscus, T=tibia), and the scale bar represents 200 μM. (f) Number of osteophytes per section were calculated from Safranin 0/Fast Green stained sections. (g) Volume of calcified meniscus was calculated using Amira.

The therapeutic effects of oligofructose observed in our model were initiated by microbial changes in the gut, potentially through proliferation of beneficial microbes including *Bifidobacterium pseudolongum*, and/or through reductions of microbes associated with inflammation. In obese/T2D mice, *B. pseudolongum* were increased over 1,000-fold, by far the largest fold change observed of any bacteria (FIGS. 1 and 2). These microbes have previously been reported to decrease inflammation in obesity/T2D, lending to their beneficial classification. In all analyzed tissues, an elevated inflammatory signature with obesity/T2D was observed, and subsequent reduction following oligofructose supplementation. Circulating serum inflammatory cytokines and chemokines including KC, MIP-1B, M-CSF, and TNF were increased with obesity/T2D, and reduced to baseline levels with oligofructose (FIG. 3). These data corroborate with joint specific changes, where total number of cells as well as F4/80 positive infiltrating macrophages were significantly increased in the synovium of obese/T2D mice, and reduced by oligofructose. This reduction of hyperplastic synovial tissue was accompanied by reduced levels of TNF when obese/T2D mice were supplemented with prebiotics (FIGS. 4 and 6). Inflammatory cytokines in the joint often lead to chondrocyte hypertrophic changes, including production of MMP13 and ColX. In obese/T2D mice, MMP13 and ColX were both increased in uncalcified cartilage compared to lean, an effect that was again rescued by oligofructose, indicating the prebiotic was able to block terminal hypertrophy of chondrocytes, lending to its chondroprotective effect (FIG. 6).

Fracture Repair

Previously, it was demonstrated that delayed tibial fracture healing in obese/T2D mice was associated with biomechanical deficits and markedly increased callus size due to delayed callus remodeling as well as robust callus adiposity. (Brown et al. 2014 *PLoS One* 9(6):e99656.)

As demonstrated here, the prebiotic oligofructose reverses both the increase in callus size and adiposity that are characteristic of the obese/T2D mouse fracture phenotype (FIG. 10A-10E). With oligofructose, callus characteristics in the obese/T2D mice are indistinguishable from those of lean mice, and these changes are associated with marked alterations in the gut microbiome. One commensal bacteria, *Bifidobacterium pseudolongum*, a well-known anti-inflammatory microbe, dominates the gut microbiome following oligofructose supplementation. Concurrently, several gut microbial species that are linked to inflammatory states, including *Lactobacillus helveticus* and *Staphylococcus sciuri*, are suppressed by oligofructose (FIG. 10H).

Figure 10:
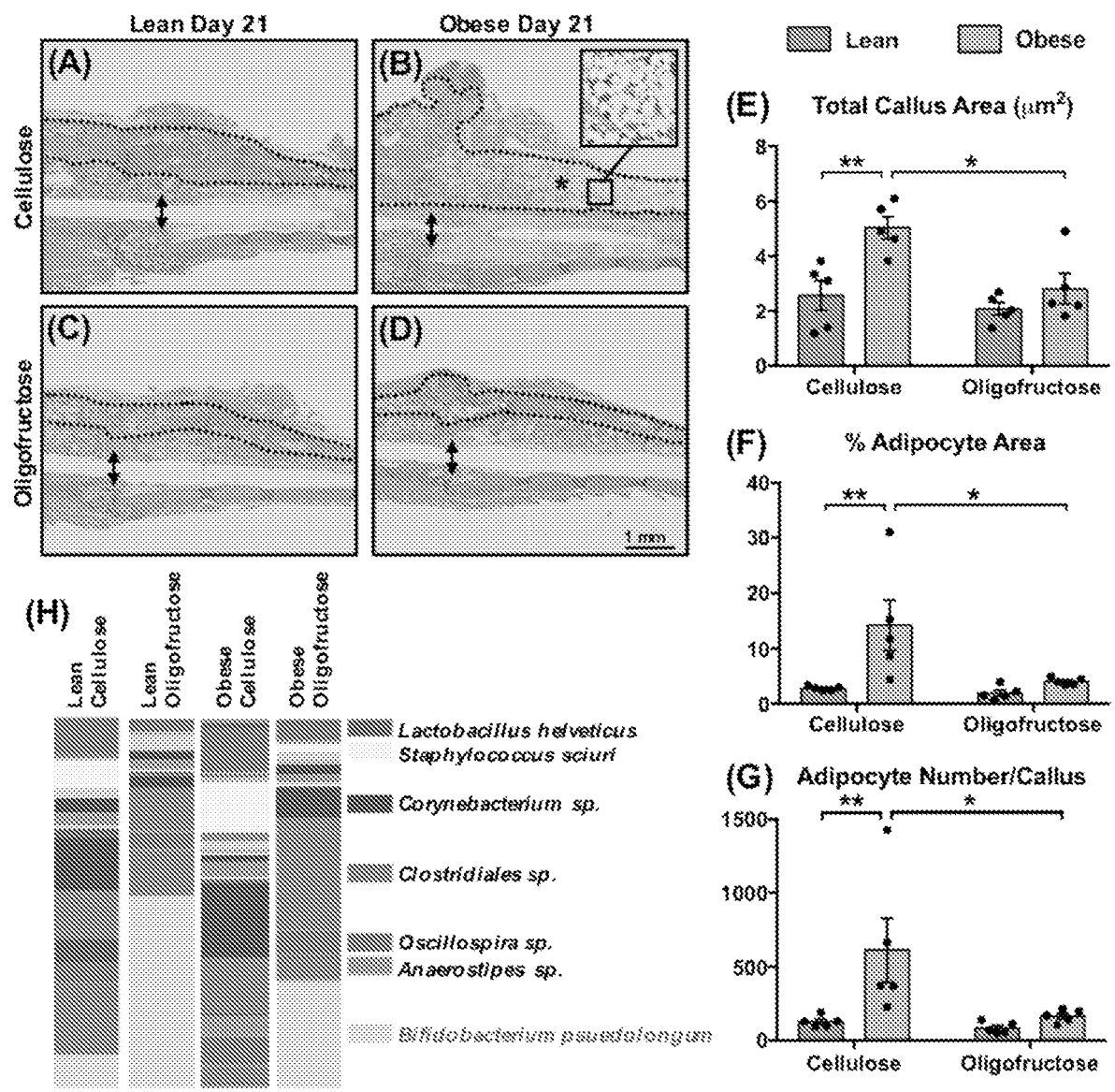
FIG. 10: Oligofructose rescue of impaired fracture healing in obese/T2D mice is associated with restoration of a healthy gut microbial profile. A-D. Representative sections for each experimental group reveal increased callus size and adiposity at the day 21 time point (i.e., persistent callus), with rescue of these phenotypes in oligofructose-supplemented mice. Arrows denote the fracture site, the dotted line outlines the callus on the anterior tibial cortical surface, the asterisk demarcates an area crowded with adipocytes, and the box and inset shows a high magnification view of local callus adipocytes in the obese/T2D sample. E-G. Histomorphometry results revealed increased total callus area and adiposity and correction of this phenotype in mice supplemented with oligofructose (*p<0.05, **p<0.01, N=5-6, ANOVA with a Tukey's multiple comparison post-test). H. rDNA sequencing analysis reveals population changes in gut microbial species, with *B. pseudolongum* (light blue) lost in obesity/T2D and restored in mice supplemented with oligofructose.
Figure 11:
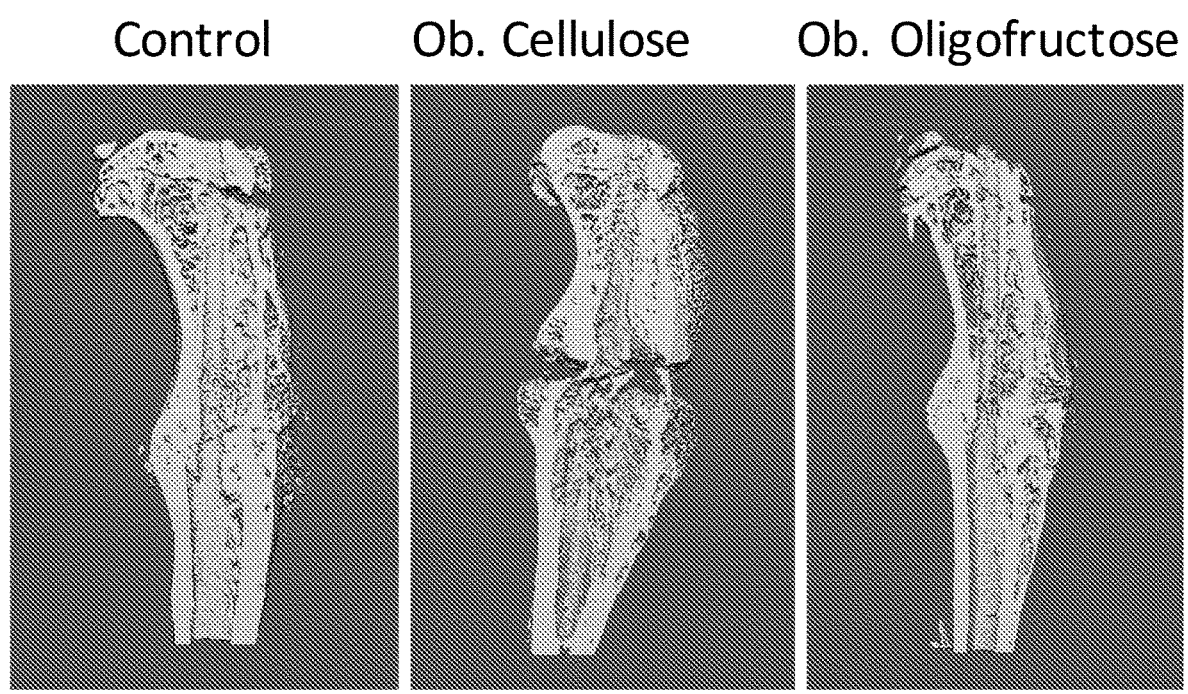
FIG. 11: Oligofructose rescue of delayed union in obesity and associated type 2 diabetes. Representative pCT scans for each experimental group at the day 21 post fracture, demonstrating delayed fracture union in obese mice supplemented with cellulose (control). This was rescued by the addition of oligofructose in high fat-fed obese mice.

These results suggest that oligofructose can revert the pro-inflammatory obese/T2D gut microbiome into the state seen in lean-fed healthy mice, concomitantly rescuing the fracture callus architecture and adiposity defects that are associated delayed fracture repair in obesity/T2D (FIGS. 10F and 10G). Also demonstrated for the first time is that manipulation of the gut microbiome can have a downstream impact on the cascade of events that play out during the fracture healing process, rescuing the delay in fracture union in obesity/T2D (FIG. 11). More specifically, our data suggest that impaired fracture repair in obesity/T2D is linked to an inflammatory process driven by an altered gut microbiome that can be addressed by restoring a healthy microbial profile using prebiotic strategies. The implications are clinically important given the simplicity of this candidate treatment to deal with a clinical problem that is without a globally accepted therapeutic strategy short of aggressive endocrine and surgical interventions.

In the absence of oligofructose (cellulose-fed control), HFD-induced obesity/T2D was associated with a larger fracture callus based on histomorphometry (FIG. 11A-11E), suggesting delayed remodeling of the callus at this 21-day time point. There was also a marked increase in callus adiposity compared to lean-fed mice (FIGS. 11A-D and 11F) that was significant based on histomorphometric quantification of both % adipocyte area (FIG. 11F) and adipocyte number (FIG. 11G). Remarkably, in parallel groups provided oligofructose along with the high fat diet, callus architecture, size and adiposity were normalized to the phenotype observed in lean-fed mice based on tissue architecture (FIG. 11A-11D), % adipocyte area (FIG. 11F), and adipocyte number (FIG. 11G). Moreover, the delay in union seen in RFD-cellulose mice (FIG. 12) was rescued by supplementation with oligofructose. Together, the results indicate that oligofructose rescues delayed fracture healing and callus adiposity in obesity/T2D.

Immune Response to Bacterial Infection

Figure 7:
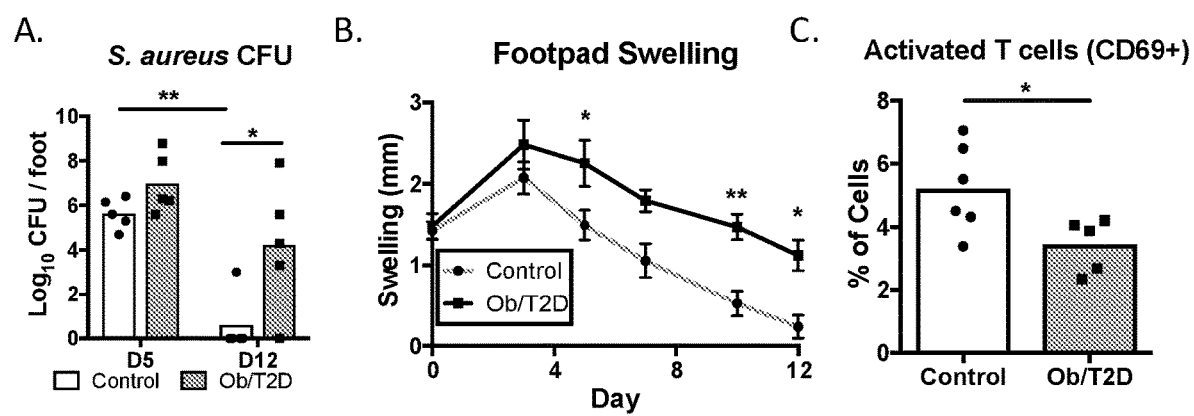
FIG. 7: Increased *S. aureus* persistence in obese/T2D mice. C57B16/J mice were fed a high fat-diet (60% Kcal from fat) for three months or a control diet (10% Kcal from fat). Mice were then infected in the footpad with *Staphylococcus aureus*. A. At day 5 and 12, mice were sacrificed, and infected feet were isolated, homogenized, and plated on agar plates for CFU enumeration. B. Footpad swelling was tracked over the duration of the experiment, demonstrating increased immune cell infiltration. C. At day 12, draining popliteal lymph nodes were isolated, and stained for flow cytometry using CD3 (T cells), CD4 (T helper cells), and CD69 (early activation marker). *$p<0.05$, **$p<0.01$.
Figure 8:
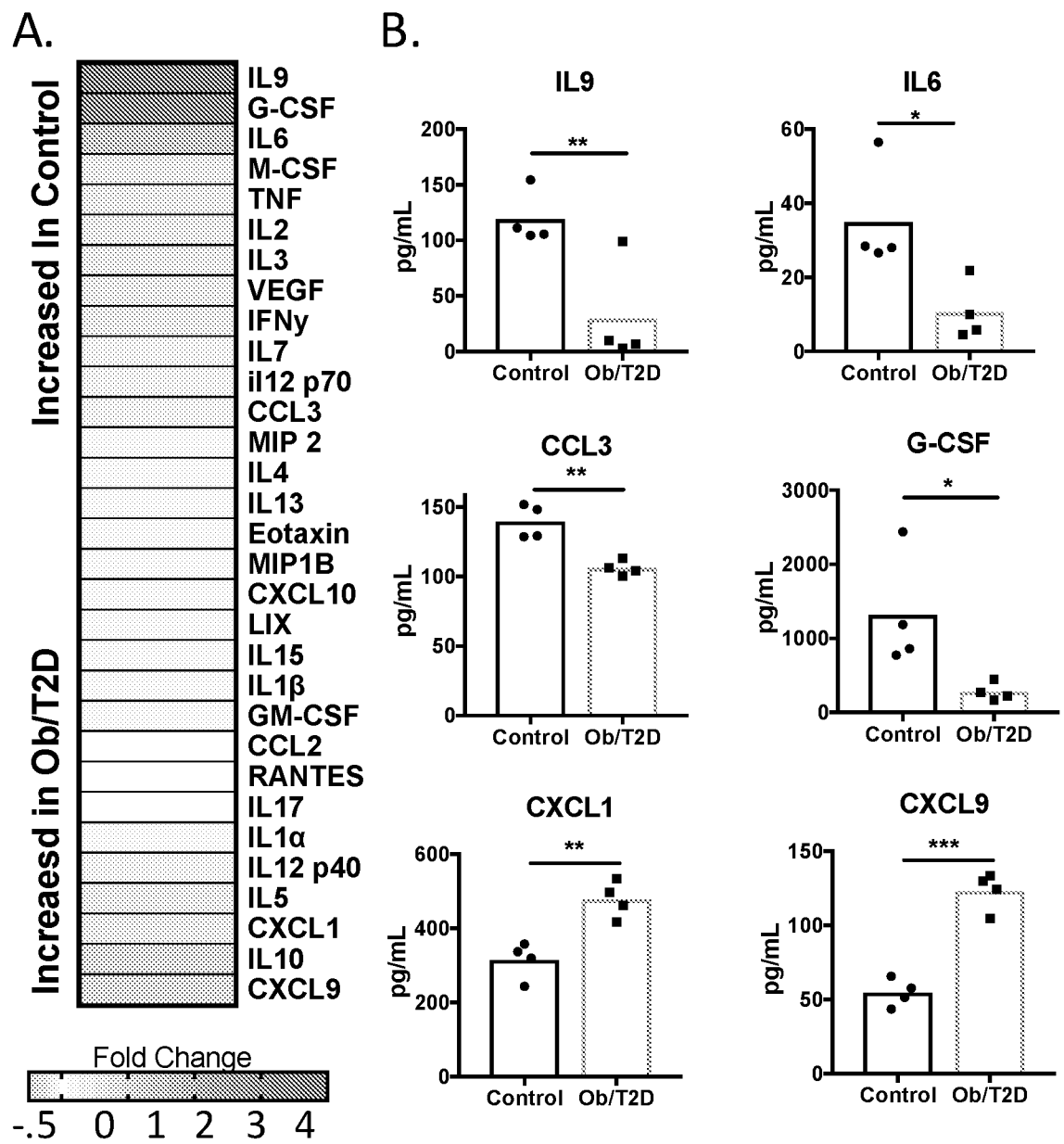
FIG. 8: Altered cytokine production by obese/T2D mice following *S. aureus* infection. Serum was collected 5 d post-infection from control and obese mice infected in the footpad with *S. aureus*. A. Heat map indicating changes in cytokines between control and obese mice. Red indicates an increase in control, and green indicates a relative increase in obese mice. B. Significantly changed cytokines between control and obese mice from A. Several cytokines primarily produced by macrophages are decreased in obesity/T2D, including IL-6, CCL3, and G-CSF. Cytokines that recruit inflammatory neutrophils and CD8 T cells are increased in this population (CXCL1 and CXCL9). *$p<0.05$, $p<0.01$, *$p<0.001$).
Figure 9:
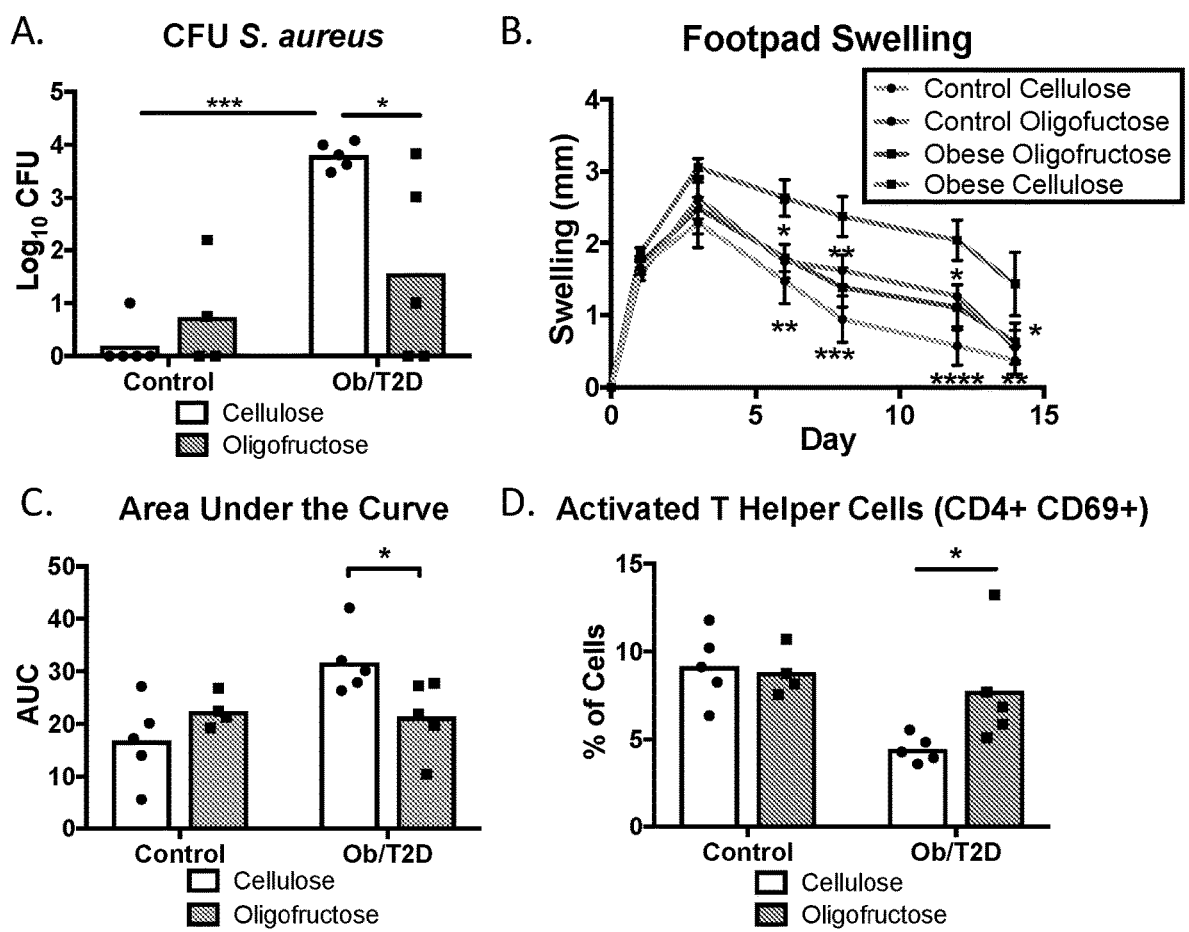
FIG. 9: Oligofructose supplementation rescues impaired *S. aureus* clearance and reduced immune responses in obese/T2D mice. C57B16/J mice fed a high fat-diet (60% Kcal from fat) or a control diet (10% Kcal from fat) were switched to control or high fat-diets containing cellulose (control) or oligofructose. Mice were then infected in the footpad with *S. aureus*. A. At day 14 post-infection, mice were sacrificed, infected feet were isolated, homogenized, and plated on agar plates for CFU enumeration B. Footpad swelling, reflecting immune cell infiltration to the infection site, was tracked over the duration of the experiment. Obese mice had increased infiltration but decreased bacterial clearance compared to lean mice. Oligofructose rescued this defect in obese mice. C. Area under the curve measurements from B. D. Draining popliteal lymph nodes were isolated at d14 and analyzed by flow cytometry for CD4+CD69+T helper cells, a subset of cells that are crucial for *S. aureus* clearance in chronic infection. *p<0.05, p<0.01, * p<0.001. **** p<0.0001.

Demonstrated here in a foot infection model is that obesity/T2D is associated with increased immune cell infiltration and impaired clearance of the *Staphylococcus aureus* (FIGS. 7A-7B). Moreover, there is a decrease in T helper cell activation within the draining popliteal lymph nodes 12 d post-infection (FIG. 8C). This effect is associated with dysregulation of key cytokines and chemokines in obesity/T2D (FIG. 9A), including IL-9, Il-6, CCL3, and G-CSF (FIG. 9B). Obese/T2D mice whose diet was supplemented with oligofructose (10% w/m) had increased clearance of *S. aureus* from the foot, indicating improved immune responses (FIG. 10A). Consistent with this, oligofructose supplemented obese/T2D mice had a significant reduction in immune cell infiltration compared to obese/T2D cellulose (control) mice, almost to that of lean-fed control mice (FIG. 10B-10C). The draining popliteal lymph node, a site of adaptive immune responses, was also isolated and immune cells were enumerated by flow cytometry. Obese/T2D mice supplemented with cellulose had impaired T helper cell activation, indicating reduced innate and humoral immune responses (FIG. 10C). Supplementation of obese/T2D mice with oligofructose rescued this impairment to that of lean levels. Taken together, the results showed that oligofructose corrects impaired immune responses in obesity/T2D to that of lean-fed control mice.

Previously demonstrated was an increase in bacterial burden in obese/T2D mice following orthopaedic implant associated infection. Demonstrate here in a model of foot infection is that diet-induced obesity/T2D is associated with an impaired ability to clear bacteria from the infection site (FIG. 7A). These results further validate clinical studies indicating obesity/T2D as a risk factor for infection. (Farnsworth et al. 2015 *Infection and immunity* 83(6):2264-74; Winfield et al. 2016 *The American surgeon* 82(4):331-6.)

This clinically relevant model of infection recapitulates a diabetic footpad infection. Defective clearance of the infection indicates impairment in immune responses in obesity. This is consistent with an increase in footpad swelling in obese/T2D mice, demonstrating an influx of immune cells to the site of infection (FIG. 7B), and reduced T helper cell responses in the draining popliteal lymph nodes (FIG. 7C). Elevated inflammation and impaired *S. aureus* clearance within the footpad was also associated with an alteration in cytokine responses in obese/T2D mice (FIG. 7A). Despite increased immune cell infiltration, several cytokines known to be secreted by macrophages, including IL-6, CCL3, and G-CSF were all reduced systemically in obesity/T2D (FIG. 8B), while cytokines associated with CD8 T cell and neutrophils were increased systemically in obesity/T2D. Taken together, these results demonstrate an impairment of the innate immune response in obese/T2D mice to infection.

Mice on a high fat-diet display a proinflammatory gut microenvironment. To test how alteration of the gut microbiome alteres immune function, mice on a lean, or high-fat diet were supplemented with either control cellulose or oligofructose. Supplementation with oligofructose markedly altered the gut microbiome in obese/T2D mice, shifting towards a more anti-inflammatory profile (FIGS. 1 and 2). Importantly, oligofructose corrected the systemic inflammation associated with obesity/T2D (FIG. 3A-3E). A reduction in chronic inflammation in obese/T2D, oligofructose treated mice was associated with a significant improvement in *S. aureus* clearance 14 days post infection (FIG. 9A). This was associated with normalization in immune cell infiltration in obese/T2D oligofructose mice to that of lean controls (FIGS. 9B-9C) and improved activation of helper T cells in the draining popliteal lymph nodes (FIG. 9D). Taken together, these results suggest that oligofructose can improve systemic inflammation associated with obesity/T2D, improving bacterial clearance and lymphocyte function in the scenario of an infection. These findings are clinically important, as the only current treatment to improve immune function in obese/T2D patients is to reduce BMI. Weight loss is a slow process, and is often associated with patient non-compliance. Importantly, the effects seen in improved immune responses in mice supplemented with oligofructose occurred after only two weeks of treatment. These results suggest that supplementation with oligofructose in obese/T2D and morbidly obese/T2D patients can correct impairments in immune functions, effectively reducing the risk of infections.

Using information gathered from studies documented herein, the envisioned technology combines typical doses of oligofructose (1-20 gm/dose) combined with $10^7$-$10^{11}$ colony forming units of a mixed culture of *Bifidobacterium*, or a pure culture of *Bifidobacterium pseudolongum*, that could be delivered as a mixture in a drink, could be combined into a food product (e.g., yogurt), or could be processed into tablet or capsule forms. The supplementation regimen would encompass consuming the combination formulation one time/day, three times per week, two times per week, or one time per week.

Applicant's disclosure is described herein in preferred embodiments with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of Applicant's disclosure may be combined in any suitable manner in one or more embodiments. In the description herein, numerous specific details are recited to provide a thorough understanding of embodiments of the invention. One skilled in the relevant art will recognize, however, that Applicant's composition and/or method may be practiced without one or more of the specific details, or with other methods, components, materials, and so forth. In other instances, well-known structures, materials, or operations are not shown or described in detail to avoid obscuring aspects of the disclosure.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples disclosed herein are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. The following examples contain important additional information, exemplification and guidance that can be adapted to the practice of this invention in its various embodiments and equivalents thereof.

What is claimed is:

1. A method for treating osteoarthritis, comprising:
administering to a human subject in need thereof a composition comprising oligofructose and microbes from the genus Bifidobacteria in an amount effective to treat osteoarthritis, wherein the oligofructose is characterized by a non-digestible dietary fiber suitable for increasing specific bacteria under the genus Bifidobacteria in the gastrointestinal tract, and wherein the Bifidobacteria comprises *Bifidobacterium bifidum, breve, longum, animalis, lactis,* and *infantis*.

2. The method of claim 1 wherein the osteoarthritis is associated with obesity and/or type 2 diabetes.

3. A method for improving joint health or bone health, comprising:
  administering to a subject in need thereof oligofructose and microbes from the genus Bifidobacteria, in a single composition or in separate compositions, wherein the oligofructose is characterized by a non-digestible dietary fiber suitable for increasing specific bacteria under the genus Bifidobacteria in the gastrointestinal tract, in amounts effective for improving joint health or bone health, and wherein the Bifidobacteria comprises *Bifidobacterium bifidum, breve, longum, animalis, lactis,* and *infantis*.

4. The method of claim 3, wherein the oligofructose is administered daily, thrice weekly, twice weekly, or weekly, and/or the microbes from the genus Bifidobacteria are administered daily, thrice weekly, twice weekly, or weekly.

* * * * *